United States Patent [19]

Saaski et al.

[11] Patent Number: 5,039,491
[45] Date of Patent: Aug. 13, 1991

[54] OPTICAL OXYGEN SENSOR

[75] Inventors: Elric W. Saaski, Bothell; David A. McCrae, Seattle; Dale M. Lawrence, Lynnwood, all of Wash.

[73] Assignee: MetriCor, Inc., Woodinville, Wash.

[21] Appl. No.: 303,444

[22] Filed: Jan. 27, 1989

[51] Int. Cl.$^5$ .................. G01N 21/00; A61B 5/00; G02B 5/00
[52] U.S. Cl. .................. 422/82.05; 422/82.03; 422/82.04; 436/136; 436/138; 128/633; 128/634; 356/436; 356/440; 359/838
[58] Field of Search .................. 356/51, 437, 440, 441, 356/445, 448; 364/413.09; 128/633, 634; 436/136, 138; 422/55, 58, 60, 82.03, 82.04, 82.05; 350/628, 642

[56] References Cited

U.S. PATENT DOCUMENTS

| Re. 31,879 | 5/1985 | Lubbers et al. | 69/45 |
|---|---|---|---|
| 2,806,023 | 9/1957 | Wenker | 534/876 |
| 3,202,652 | 8/1965 | Meininger et al. | 534/642 |
| 3,446,565 | 9/1969 | Rigod | 431/70 |
| 4,003,707 | 1/1977 | Lübbers et al. | 128/634 |
| 4,016,761 | 4/1977 | Rozzell et al. | 374/161 |
| 4,029,597 | 6/1977 | Neisius et al. | 436/163 |
| 4,041,932 | 8/1977 | Fostick | 128/633 |
| 4,118,485 | 10/1978 | Eriksson et al. | 514/56 |
| 4,140,393 | 2/1979 | Cetas | 374/161 |
| 4,210,029 | 7/1980 | Porter | 73/705 |
| 4,249,076 | 2/1981 | Bergstrom et al. | 250/227.23 |
| 4,268,170 | 5/1981 | Flint | 350/642 |
| 4,272,484 | 6/1981 | Lübbers | 128/633 |
| 4,272,485 | 6/1981 | Lübbers | 128/633 |
| 4,275,296 | 6/1981 | Adolfsson | 250/227.21 |
| 4,306,877 | 12/1981 | Lübbers | 128/633 |
| 4,307,607 | 12/1981 | Saaski et al. | 374/161 |
| 4,316,388 | 2/1982 | Miller et al. | 374/161 |
| 4,329,058 | 5/1982 | James | 356/352 |
| 4,356,396 | 10/1982 | Ruel et al. | 250/226 |
| 4,367,040 | 1/1983 | Goto | 356/44 |
| 4,428,239 | 1/1984 | Johnston | 73/705 |
| 4,437,761 | 3/1984 | Kroger et al. | 356/44 |
| 4,446,366 | 5/1984 | Brobardh et al. | 250/227.23 |
| 4,487,206 | 12/1984 | Aagard | 128/667 |
| 4,498,004 | 2/1985 | Adolfsson et al. | 250/227.21 |
| 4,509,522 | 4/1985 | Manuccia et al. | 128/634 |
| 4,617,608 | 10/1986 | Blonder et al. | 361/291 |
| 4,659,548 | 4/1987 | Gubbay et al. | 350/642 |
| 4,678,904 | 7/1987 | Saaski | 250/227.27 |
| 4,682,500 | 7/1987 | Kuzutaka et al. | 73/705 |
| 4,741,603 | 5/1988 | Miyagi et al. | 350/357 |
| 4,780,372 | 10/1988 | Tracy et al. | 350/642 |

OTHER PUBLICATIONS

Silacon as a Mechanical Material, Proceeding of the IEEE, vol. 70, No. 5, May, 1982 by Kurt Peterson.
Field Assisted Glass Sealing, Electrocomponent Science & Technology, 1975, vol. 2, No. 1, pp. 45–53 by George Wallis.
Reference Cited in Office Action 03/02/89–Patent No. 4,678,904 as Patent No. 4,628,904 (Double Patenting).
Windholz et al., *The Merck Index* 1983, p. 1431.

*Primary Examiner*—Robert J. Warden
*Assistant Examiner*—Theresa A. Trembley
*Attorney, Agent, or Firm*—Seed and Berry

[57] ABSTRACT

An oxygen sensor contains an indicator whose change in absorption is a function of the concentration of oxygen in a sample bathing the indicator. Light transmitted and reflected through the indicator of the sensor undergoes an absorption that is characteristic of the concentration of oxygen. The indicator is a viologen whose absorption returns to a steady-state value after it has been subjected to a pulse of short-wavelength light. The rate at which the absorption returns to the steady-state value is a function of the concentration of oxygen bathing the viologen indicator. A measurement system for use with the pO$_2$ sensor causes a short-wavelength flash to be sent to the sensor and thereafter monitors the time-varying absorption of the sensor to measure the oxygen content of the sample bathing the viologen indicator.

23 Claims, 7 Drawing Sheets

OPTICAL OXYGEN SENSOR

DESCRIPTION

1. Technical Field

This invention relates to oxygen sensors and a system for their use, and more particularly, to oxygen sensors in which the optical absorption of an indicator is a function of the concentration of oxygen to which the indicator is exposed.

2. Background Art

Modern-day diagnosis and treatment of patients undergoing surgery and other, critically ill, patients often require the measurement of blood gases, such as $pO_2$ in blood. These blood gases are regarded as critical measures in the clinical assessment of pulmonary and cardiovascular function.

Current hospital practice for measuring the oxygen concentration in a patient's blood is both time-consuming and expensive. A sample of the patient's blood must be specially prepared and treated before it is sent to a dedicated blood gas analysis instrument within the hospital laboratory. While this instrument performs the blood analysis quickly, significant time delays occur in taking the sample to the analysis instrument and returning with the analysis results. Although some of the time lost by processing the blood samples at a remote location has been regained by placing blood gas analyzer instruments in or near surgical and other critical care units, these instruments are expensive and require the assignment of specially trained laboratory personnel.

A variety of methods for making bedside blood oxygen measurements have been proposed. The transcutaneous method, which measures blood oxygen through the skin, is not accurate when used with adult patients. Direct contact measurements, made by sensors placed within the vascular system or by bringing blood to sensors outside the patient's body, have also been proposed. Miniature electrochemical sensors have proven to be unstable and expensive. Miniature gas chromatographs or mass spectrometers are expensive to build, service, and maintain. Some miniature optical-based systems rely on fluorescence. Fluorescent systems operate typically at short wavelengths and have low return light levels. These systems are difficult to implement with solid-state hardware.

It would be particularly useful, then, to have a system for measuring the concentration of oxygen in the blood that is based on changes in the absorption/transmission of specific chemical indicators that operate at longer wavelengths and that can be supported by cost-effective, solid-state electronics. Additionally, it would be useful to have optical concentration sensors that are inexpensive and thus disposable after a single use.

Although the inventive oxygen sensor described herein is used primarily for measuring the oxygen concentration in blood, it will be understood that the invention is applicable to the measurement of oxygen concentrations for any purpose.

SUMMARY OF THE INVENTION

It is an object of the present invention to provide an electro-optical sensor for measuring the concentration of oxygen in a substance based upon changes in the optical absorption characteristics of a chemical indicator when exposed to oxygen.

It is another object of the present invention to provide an oxygen sensor that operates at optical wavelengths that are compatible with solid-state electronics.

It is still another object of the present invention to provide an optical measurement system for use with optical absorption/transmission oxygen sensors.

A sensor of the present invention includes an indicator chamber containing an indicator that receives radiation having predetermined color characteristics. An aperture opening into the indicator chamber allows the substance being analyzed to enter the indicator chamber. The indicator has radiation-absorption characteristics that change when the indicator is exposed to oxygen. More specifically, the indicator chosen is one in which radiation absorption/transmission characteristics at a first wavelength change during or after being illuminated with light at a second wavelength. The rate at which the absorption/transmission characteristics change is a function of the concentration of oxygen to which the indicator is exposed. An example of such an indicator is one of the class of compounds called "viologens." A light-measuring unit is provided for receiving reflected radiation and generating a signal indicative of the concentration of oxygen in the substance being analyzed. In operation, the optical measurement system first sends a pulse of light at the second wavelength to the indicator in the sensor. The absorption/transmission of the indicator for the first wavelength waveband of light then markedly increases. The rate at which the absorption/transmission characteristics change for the light at the first wavelength is a function of the concentration of oxygen to which the indicator is exposed.

DETAILED DESCRIPTION OF THE INVENTION

Figure 1:
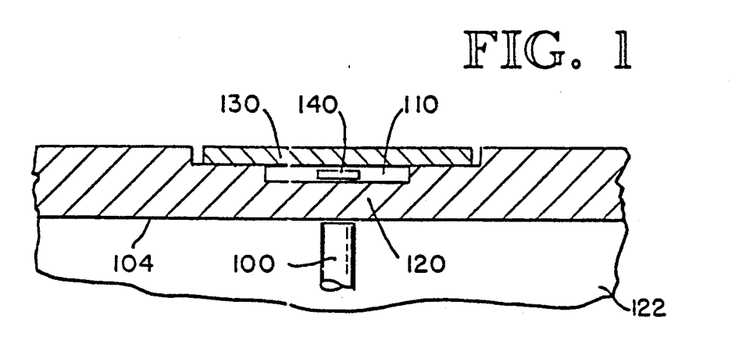
FIG. 1 is a schematic view of an oxygen sensor of the present invention.

The key features of the oxygen sensor are shown in FIG. 1. The sensor receives radiation having predetermined color characteristics, typically produced by a light-emitting diode (LED) with a peak wavelength in the 600-700 nm (i.e., red) range. The sensor has a light-measuring unit operative for receiving reflected radiation and for generating a corresponding signal indicative of the concentration of the substance being analyzed. The radiation is delivered to and channeled from the miniature indicator chamber 110 via optical fiber 100 in base 122, which is flush-mounted against the transparent substrate 120. The indicator chamber 110 is formed by the transparent substrate 120 and a radiation-reflective wall 130. In an alternative embodiment, the radiation can be supplied to the sensor from an LED built into the base 122 for the sensor and the reflected radiation can be detected by photodiodes also built into the base 122.

Figure 2:
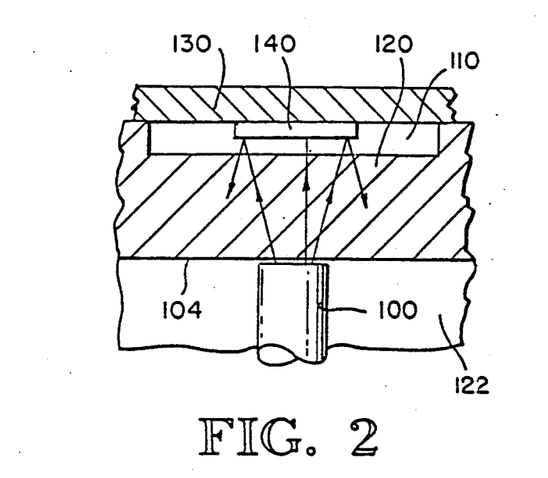
FIG. 2 is a schematic view of an oxygen sensor having the indicator affixed to the reflective wall.
Figure 3:
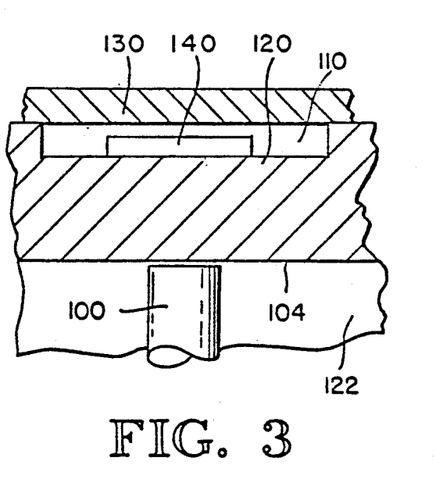
FIG. 3 is a schematic view of an oxygen sensor having the indicator affixed to the a transparent substrate.
Figure 4:
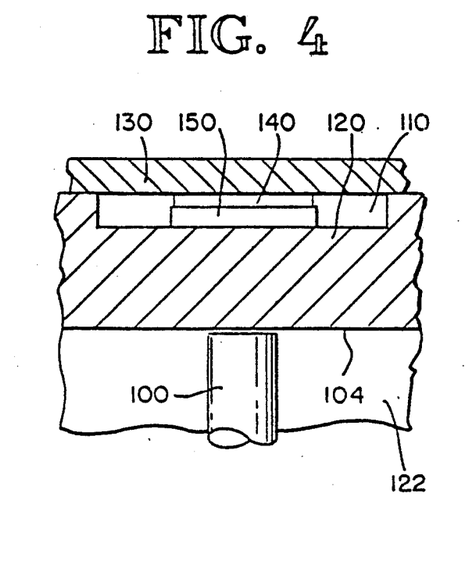
FIG. 4 is a schematic view of an oxygen sensor having the indicator affixed to a supporting means within the indicator chamber.
Figure 5:
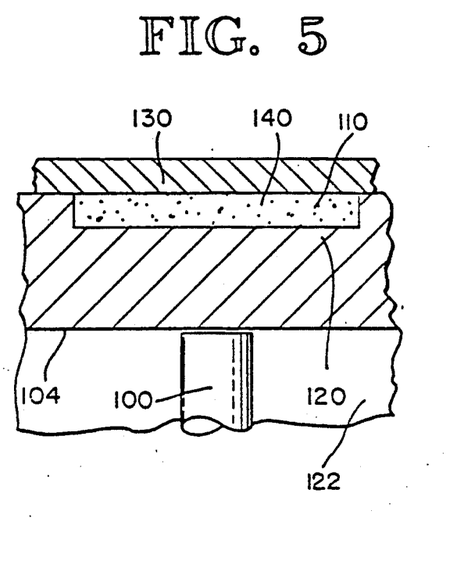
FIG. 5 is a schematic view of an oxygen sensor having the indicator admixed in the backfill material.

Radiation enters and exits the indicator chamber via the transparent substrate 120. The radiation-reflective wall 130 is positioned opposite the source of radiation so that the radiation is reflected back to the light-measuring unit. The sensor contains an indicator 140 that may be positioned within indicator chamber 110 in a variety of ways. For example, as shown in FIG. 2, indicator 140 may be affixed to reflective wall 130 inside indicator chamber 110. Similarly, as shown in FIG. 3, indicator 140 may be affixed to transparent substrate 120 within indicator chamber 110. Instead of attaching indicator 140 to a wall of indicator chamber 110, indicator 140 may be affixed to a supporting means 150, such as a button, which is positioned within indicator chamber 110, as shown in FIG. 4. Finally, as FIG. 5 illustrates, the indicator 140 may be admixed with backfill material contained in indicator chamber 110.

Indicator chamber 110 is constructed within transparent substrate 120, which is made from a transparent material capable of being formed into thin sheets, and, for example, may be plastic, Corning code 7740 glass, or quartz glass. Chamber 110 may be formed either by embossing the cavity into the surface of the transparent substrate 120 or by etching with solutions containing hydrofluoric acid. The wet chemistry methods are particularly useful in that they enable precision positioning and control of the depth of the chamber. Typical depths of the indicator chamber range from 10 to 50 microns.

For many applications, it is necessary that the sensor respond quickly to a change in its sensed environment. A basic purpose of this design is to produce low-cost yet reliable sensors having very small physical dimensions and rapid response times.

A key component of the present invention is reflective wall 130 of the indicator chamber 110. Reflective wall 130 is a mirror that reflects radiation back toward a light-measuring unit. The mirror must have high long wavelength reflectivity to maximize the returned light. In addition, the mirror should have satisfactory UV reflectance to assist in uniformly radiating the indicator by reflecting unabsorbed UV light for a second pass through the indicator 140. Finally, the positioning of the mirror significantly affects the ability of the sensor to track rapidly changing gas conditions in a fluid sample, such as blood. Decreased sensor response speed is caused by the mirror shrouding the indicator from the surrounding fluid environment.

Figures 6, 7, 8:
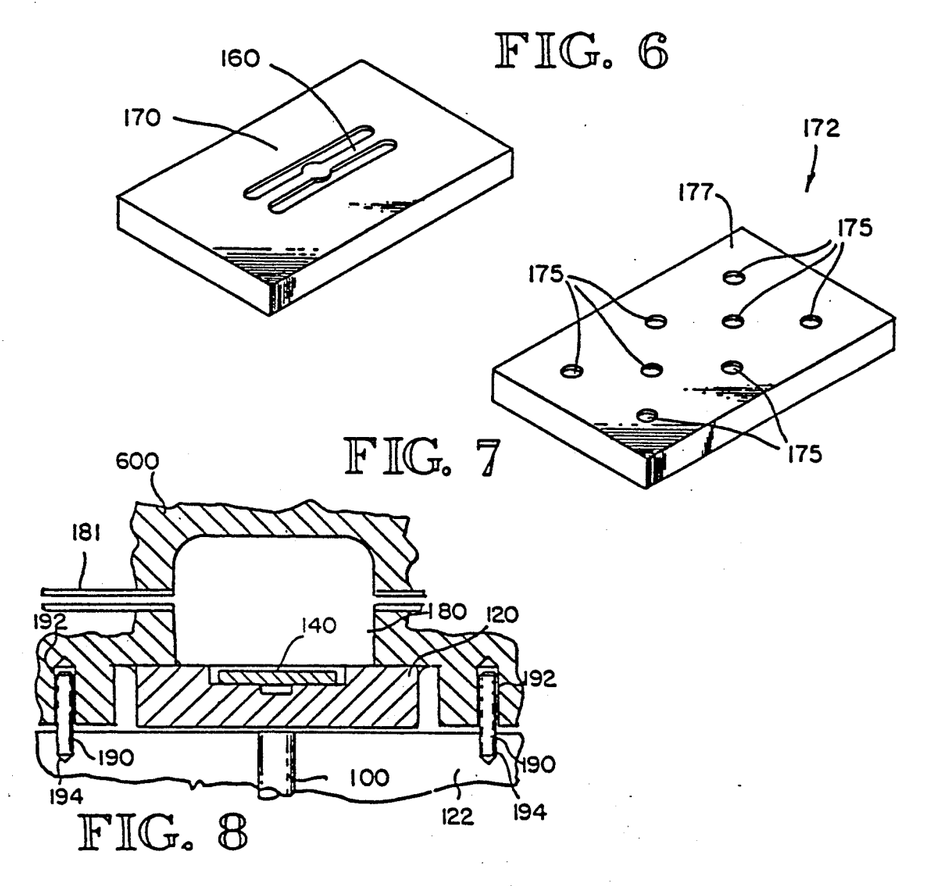
FIG. 6 is a perspective view of a mirror having two apertures.
FIG. 7 is a perspective view of a mirror having a plurality of apertures.
FIG. 8 is a schematic view of an oxygen sensor including a liquid sample chamber.

Two alternative mirror designs are shown in FIGS. 6 and 7. The mirror of FIG. 6 has a central reflecting bar 160 with chamber-accessing slots on each side. An additional ring of material 170 is formed at the center of the reflecting bar 160, protecting reflecting bar 160 and adding significant rigidity to the structure. This mirror shape can be generated in thin glass or plastic, but preferably, in 4- to 25-micron thick, single-crystal silicon by using standard wet chemistry micromachining methods. The mirror reflective surface is obtained by coating the polished silicon face with a highly reflective, noncorroding material, such as gold; a nonmetallic, multilayer, dielectric mirror coating may also be used. The resulting mirror is exceedingly thin, highly reflective, non-corroding, and extremely strong—this being the result of using single-crystal silicon. The use of a silicon membrane mirror is also of significant advantage in that the lateral dimension of reflecting bar 160 can be very precisely defined and the mirror made so thin that the channels on each side of the bar do not generate a significant secondary diffusion barrier.

An alternative mirror design is shown in FIG. 7. In this approach, anisotropic silicon etching techniques are used to generate a "porous" silicon mirror 172 that has a plurality of microminiature holes 175 through the reflective silicon membrane 177. This allows more rapid communication of the gas with the indicator and results in a shorter diffusion length and faster sensor equilibration. Commercially available, thin-film porous media may also be employed if the surface facing the cavity has deposited on it a reflective layer. The reflective media must not severely fill the film's pores so as to restrict diffusive transport. As a general rule, the mirror should be at least 10% porous on an area basis and the size of an individual pore should not exceed about ⅛ of the diameter of the core of the optical fiber. Typical core diameters are on the order of 0.004 inches, although core diameters of commercially available optical fibers can vary considerably from 0.004 inches. Larger pores will also work, but significant differences in reflected light levels will be found from sensor to sensor if the reflector is not essentially a homogeneous surface. If larger pores are acceptable, then the mirror may be made from other reflective materials, such as metal sheets or dichroic layers, using similar, but isotropic, etching processes. It is also desirable to fill the pores with silicone rubber or an oxygen-transmissive gel to minimize clotting and material deposition under the mirror. It may be desirable to use an optically absorbent dye or other light-absorbent media within the pores to minimize optical coupling to the external environment.

The mirror 130 is mounted directly over the indicator chamber and onto transparent substrate 120 using either anodic bonding, heat-sealing/fusion, or polymer adhesive, or by using the backfill material within the indicator chamber as an adhesive. A number of mirrors may be mounted by optically or mechanically positioning them on a substrate with a corresponding number of indicating chambers. When in the proper position, they can be fixed very rapidly with heat-sealing or with an adhesive which hardens upon exposure to an ultraviolet light source. This will be particularly useful for mass-producing the sensors. Alternatively, they can be fixed less quickly using a conventional heat-curing adhesive.

As shown in FIG. 8, transparent substrate 120 is typically mounted in a plastic cap containing a cavity 180 appropriately located so as to form a liquid sample chamber, with the substrate forming one side thereof. This cavity then communicates with external liquid or gaseous fluid samples via adhesively bonded tubes 181 mounted into the cap side walls.

Figure 9:
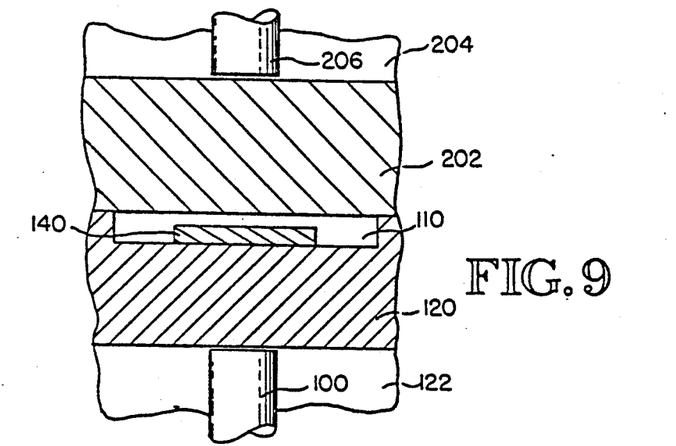
FIG. 9 is a schematic view of an alternative embodiment of an oxygen sensor in which radiation is transmitted through the sensor.

An alternative embodiment of the optical sensor, illustrated in FIG. 9, utilizes a second transparent substrate 202 instead of the radiation-reflective wall 130 used in the embodiment of FIGS. 1-5. The second transparent substrate 202 is mounted on a second base 204 through which extends a second optical fiber 206. The first transparent substrate 120 has a cavity formed therein to provide the indicator chamber 110 in which an indicator 140 is mounted. The second transparent substrate 202 is either porous or formed with apertures to permit the gas or liquid to be sensed to pass into the indicator chamber 110.

As with the embodiment of FIGS. 1-5, the indicator chamber 110 is constructed within transparent substrate 120, which is made from a transparent material capable of being formed into thin sheets, and, for example, may be plastic, Corning code 7740 glass, or quartz glass. Chamber 110 may be formed either by embossing the cavity into the surface of the transparent substance or by etching with solutions containing hydrofluoric acid. The wet chemistry methods are particularly useful in that they enable precision positioning and control of the depth of the chamber. Typical depths of the indicator chamber 110 range from 10 to 50 microns.

In operation, incoming radiation passes through the first transparent substrate 120 and the indicator 140 and into the second transparent substrate 202. The radiation passing through the second transparent substrate 202 is conveyed through the second optical fiber 206 to a measurement device.

With reference, now, to FIG. 8, alignment between optical fiber 100 and sensor 140 is accomplished by locating pins 190. The locating pins 190 are received in correspondingly shaped recesses 192, 194 formed in the cap 600 and base 122, respectively. The pins 190 allow placement of transparent substrate 120 within tolerances required for fiber sensor alignment prior to adhesive bonding of wall 120 to cap 600. They also allow the use of a mirror-positioning fixture for alignment of the sensors when they are being assembled.

To maintain measurement accuracy, the sensor 140 may have to be temperature controlled. This can be accomplished by controlling the temperature of the closely contacting base 122. The optical fiber 100 can be bundled with electrical conductors to form an umbilical cord that carries electrical current to indirectly heat the indicator 140 in indicator cavity 110.

To minimize the reflection of extraneous light from the sensor, the end of optical fiber 100 and substrate 120 must not be separated by an air gap. Filling any fiber-substrate gap 104 that exists with an index-matching material minimizes unwanted reflections. Typical index-matching materials are silicone gels or polyethylene glycols having refractive indices approximately equal to that of the fiber core (typically 1.46). The latter are favored because of their nontoxicity and because their water-solubility allows the fiber base to be easily cleaned in water or alcohol. A preferred polyethylene glycol is PEG 400.

The optical fiber can alternatively be coupled to the sensor through the use of optical elements, such as lenses. This will relax the need for the optical fiber to be butted against the substrate. Optical elements may also eliminate entirely the use of optical fibers.

The oxygen indicator 140 is a substance whose radiation-absorption characteristics change when the indicator 140 is exposed to $O_2$. Preferably, the indicator belongs to a class of compounds known as "viologens." Viologens are N,N'-disubstituted -4,4'-dipyridinium salts. When irradiated with UV light, these compounds undergo a one-electron photoreduction, the resultant radical cations having an absorption maximum near 650 nm. The radical cation is reoxidized by $O_2$ to the dication at a rate that is a function of $O_2$ concentration. The reaction rate can be determined by measuring the rate of absorption decay. The initial source of the electron for reduction appears to be either the counterion or the matrix surrounding the viologen. The reaction may be reversible to some extent, but consumes the matrix, whether solvent or solid support. However, consumption of the matrix is very slow and many measurements may be made before recalibration is required.

The oxygen sensor chemistry may be implemented in a number of ways. A viologen, such as dibenzyl viologen, may be suspended in a polar polymer, such as poly(vinyl pyrrolidone). This implementation, however, allows the viologen to diffuse away if exposed to water. Alternatively, a number of polymeric viologens may be prepared. For example, 4,4'-dipyridyl may be reacted with poly(vinylbenzylchloride) to produce insoluble poly(benzylviologenco-benzylchloride). As these polymers are highly charged and very polar, they interact appreciably with water.

The photoactive viologen film sensor is contained within the indicator chamber 110 etched into transparent substrate 120. The viologen sensor is, for example, held in place by a silicone rubber potting compound and mirror 130 that partially covers the top of the etched chamber. The optical fiber is located on the opposite face of the substrate, on axis with the indicator. Operation is as follows:

A pulse of ultraviolet light is transmitted to the indicator by the fiber, completely bathing the sensor film in ultraviolet (UV) light. The photoactive sensor film changes to a blue color, indicating a strong absorption at red wavelengths. This absorption peak decays slowly with time, taking perhaps 1 to 10 seconds, the exact rate being dependent on the oxygen concentration surrounding the sensor. The rate of absorption change is monitored with the fiber at red light wavelengths and, as will be explained subsequently, converted to an equivalent oxygen partial pressure.

The photoactive viologen sensor films used for oxygen sensing are produced by spin coating a two-part mixture dissolved in solvent onto a substrate with a commercial spinning machine (designed for photoresist coating in the semiconductor industry). The sensor films produced in this manner are very thin, generally in the range of 1 to 8 microns thick. Film thicknesses in this range are selected primarily to achieve a trade-off between high film UV sensitivity, a moderate absorbance decay rate, and film optical stability.

A thick film produces a large absorbance signal since more of the photoactive viologen is present. However, the absorbance decay rate decreases as the square of the film thickness. To lose color after a UV pulse, the viologen must react with oxygen. Once the oxygen dissolved directly in the film has been consumed, the rate of decolorization is limited by diffusion of fresh $O_2$ into the film. Hence, by adjusting film thickness, it is possible to vary the absorbance decay rate. A film thickness such that the exponential decay rate constant is between 0.10/sec and 10.0/sec is preferred for use with current supporting instrumentation systems.

As shown in FIGS. 2 through 4, the viologen films can be mounted or deposited in several ways. The viologen film may be coated on the mirror reflector or on the transmissive surface. The viologen may also be deposited on a radiation-transmissive supporting means, such as glass or plastic, which is then formed into an appropriately sized button and inserted into the indicator chamber. For use in whole blood, the chambers are then backfilled with an oxygen-permeable, transparent material, such as silicone rubber or hydrogel. The viologen may also be contained within a porous media having a reflective surface, such as soaking the media in a viologen-containing solution.

The films produced by spinning are generally cross-linked by heating in an inert gas atmosphere at 95° C. for 10-24 hours. The preferred film substrate is a thin film of gold on glass or silicon. It has been found that such viologen cross-linked films show very poor adherence to gold after short periods of immersion in saline. It has further been discovered that the inclusion of polyethylene glycols in the initial spinning mixture results in a baked film that has far superior adhesion properties, with no degradation of sensor properties. The resulting films have a mixture of viologen and glycol cross-links and are quite elastic. Optimum formulations occur when 10% to 50% of the theoretical number of cross-link positions are occupied by viologen and 10% to 40% by glycols. Polyethylene glycol of 400 average molecular weight has provided particularly good film mechanical properties.

The films, as spun and cross-linked, have also been found to leach unidentified salts which can form destructive blisters in the films under some conditions. These salts can be removed by soaking the coupons at 60-90 degrees centigrade for up to several days in dilute saline solution. As viologens are base sensitive compounds, it is advantageous to adjust the pH of this wash solution to value of pH 1 to pH 4 with hydrochloric acid. There are also secondary benefits of the leaching process. After soaking in 100 mM saline, UV sensitivity of the films is increased by as much as a factor of two. Soaking the films in solutions that are lower than 100 mM in salt at 60° to 95° C. has been found to make the film's exponential decay constant relatively insensitive to UV irradiation and to make the sensor response characteristic stable for 100 or more measurements. Also, high temperature soaking is a useful means for tailoring film sensing properties. The effects produced are stable at room temperature for extended time periods.

Two alternative methods of incorporating the viologen into the optical path may be used in the arrangement shown in FIG. 5. In one alternative, the viologen material is suspended as an emulsion phase in the backfill material, particularly silicone rubber. An advantage of this approach is that the sensor construction steps are simplified. However, the viologen and rubber should be similar in refractive index. Otherwise, the emulsion droplets act as scattering centers.

A second approach is to design a hydrophilic gel-viologen or silicone-viologen copolymer that is a single-phase, pourable media that serves the dual purposes of backfill and oxygen sensing. This approach enjoys the same advantage of ease of construction as the first approach. However, the oxygen is now so intimately dispersed in the sensing media that colorization time constants are so short that higher speed electronics may be required to observe the color decay process.

The backfill material in the indicator chamber 110 serves two purposes. First, in applications such as the measurement of blood oxygen, the backfill prevents blood cells from entering into the optical path and causing non-viologen light absorption. Second, the backfill creates a known and constant oxygen reservoir. As discussed above, the colorization decay rate is dominated by the rate of oxygen diffusion into the viologen film. This diffusion rate is dependent not only on the film properties but also on the backfill material properties, such as oxygen solubility and oxygen diffusivity. The backfill material therefore acts as an optically clear oxygen sponge drawing an equilibrium concentration of oxygen from the potentially dirty surrounding environment and creating a clean reservoir of oxygen for the viologen color decay process. Suitable materials for this function include silicone rubbers such as Petrarch PSW 1014, polycarbonate-silicone copolymers, and hydrogels.

Figure 10:
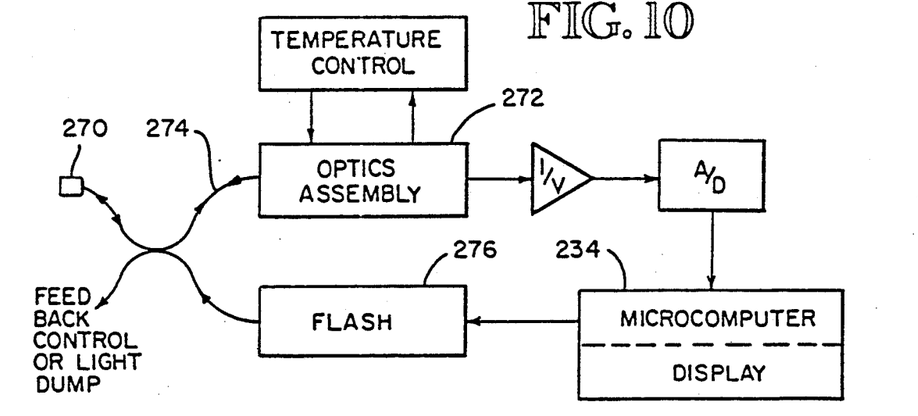
FIG. 10 is a schematic diagram of a system for measuring the concentration of oxygen in blood.

FIG. 10 is a schematic diagram of a fiberoptic $pO_2$ sensor system. $O_2$ sensor 270 is connected to the system by one or more optical fibers. Light from an LED in an optics assembly 272 is transmitted through optical fiber 274 to sensor 270. A portion of the light transmitted to sensor 270 through optical fiber 274 returns to the optics assembly 272.

Figure 11:
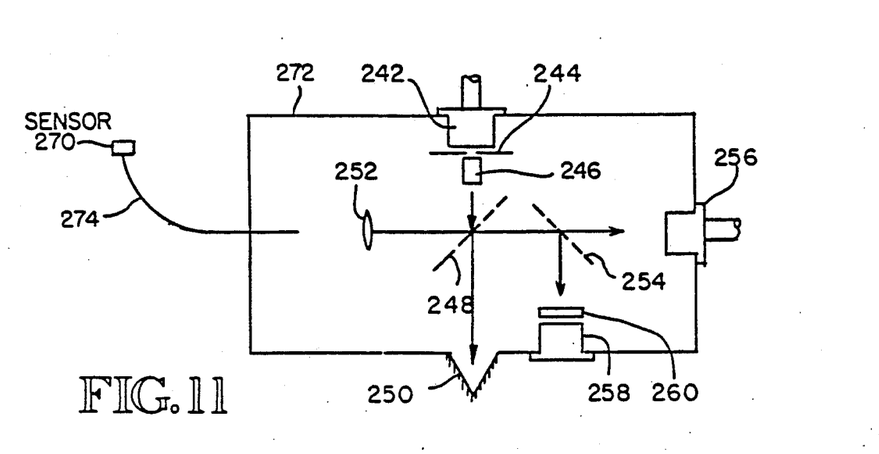
FIG. 11 is a schematic view of the optics assembly used in/the system in FIG. 10.

A schematic diagram of optics assembly 272 is shown in FIG. 11. The intensity of the light produced by LED 242 is determined by the current passing through the LED 242 which may be under the control of microcomputer 234 (see FIG. 10). LED 242 can, for example, be chosen to produce light with a peak wavelength in the range of 600 to 700 nm. The light from LED 242 passes through a pinhole aperture 244 and a ¼ pitch SELFOC lens 246 before reaching neutral beam splitter 248. Pinhole aperture 244 minimizes stray light in optics assembly 272, and SELFOC lens 246 collimates the light from pinhole aperture 244. A portion of the light striking neutral beam splitter 248 passes through to light dump 250, which can, for example, constitute a wedge-shaped cavity that has been coated with an absorptive dye. Since it is important that the light dump does not reflect light back into the optics assembly, the light dump must be very effective. A reflectivity of less than $1 \times (10^{-5})$ is desirable.

The collimated light that is reflected by neutral beam splitter 248 passes through lens 252, which focuses the pinhole image onto the end of optical fiber 274 (FIG. 11). The alignment of lens 252 with the end of optical fiber 274 is critical. Therefore, one possible configuration of these optical components is to place the lens and the end of the optical fiber into a separate assembly that allows them to be disconnected from the optics assembly. The light reflected from the lens back into the optics assembly should be minimized. Accordingly, the lens can be given an antireflection coating or highly curved surfaces. In this way, light reflected from lens 252 does not return along the same optical path as the beam formed by light returning from sensor 270 on optical fiber 274. It is also necessary to control reflections from the fiber end. To achieve this, the fiber end may be given an antireflection coating, or the lens may be designed so that the fiber directly contacts the surface of the lens and reflections are minimized by use of index-matching fluids or gels. This lens/fiber interface is available as a purchased fiberoptic connector, for example, Deutsch series 3000 fiber connector.

The light returning from sensor 270 along optical fiber 274 passes through lens 252 and on to beam splitter 254. The beam splitter may be a dichroic beam splitter or may be a neutral beam splitter. If beam splitter 254 is a dichroic beam splitter, the spectral content of the light which is transmitted through the beam splitter is different from the spectral content of the light that is reflected by the beam splitter. If beam splitter 254 is a neutral filter beam splitter, the spectral content of the transmitted and reflected light is identical. Photodiode 256 produces a photocurrent that measures the intensity of the light transmitted by beam splitter 254, while photodiode 258 measures the intensity of the light reflected by beam splitter 254. If beam splitter 254 is a neutral filter beam splitter, the reflected light can be passed through a filter 260 before reaching photodiode 258. In this case, the ratio of the photocurrents produced by photodiodes 258 and 256, respectively, is the ratio of the intensity of the returned light in the waveband defined by filter 260 to the intensity of the light produced over the entire spectrum returned from sensor 270.

If, on the other hand, beam splitter 254 is a dichroic mirror, a selected portion of the LED's waveband is transmitted to photodiode 256, while the remainder of the waveband is reflected to photodiode 258. Other spectral splitting techniques that can be used in optics assembly 272 include diffraction gratings, prisms, and combinations of all of these methods. Since the ratio of the photocurrents produced by photodiodes 256 and 258 measures only the relative magnitudes, this ratio is insensitive to connector and bending losses related to optical fiber 274. While the ratiometric technique described above is preferred it will be understood that a single photodiode measuring the intensity of the light returned from the sensor may be used.

When a $pO_2$ measurement is desired, microcomputer 234 triggers xenon flash 276. Light from the flash is transmitted to the sensor through an optical fiber. In one embodiment, the light can be transmitted through the same optical fiber as transmits the LED light, while in other embodiments, the light from the xenon flash is carried to the sensor through one or more additional fibers. When short-wavelength light (250 to 350 nm) from the flash is absorbed by the viologen in the sensor, the viologen becomes absorptive in the 550 to 750 nm wavelength range. Thus, the amount of LED light returning from the sensor at 600–700 nm decreases. Absorbance in this color range in the viologen is reversed by exposure to oxygen, and the rate of this reversal is a function of the oxygen partial pressure at the sensor. Thus, by monitoring the intensity of the returned LED light as a function of time after firing the xenon flash, it is possible to determine the partial pressure of oxygen at the sensor.

When used with the $pO_2$ sensing system of FIG. 9, optics assembly 272 uses a dichroic beam splitter 254 to transmit red LED light received from sensor 270 to photodiode 256, and light originating from flash 276, whose wavelength is between 250 and 350 nm, to photodiode 258. By integrating the current pulse produced by photodiode 258 while the xenon flash 276 (in FIG. 10) is emitting light, it is possible to obtain a measure of the total exposure of sensor 270 to light having wavelengths capable of activating the viologen. This measurement can be used to correct second-order effects in the sensor response.

Figure 12:
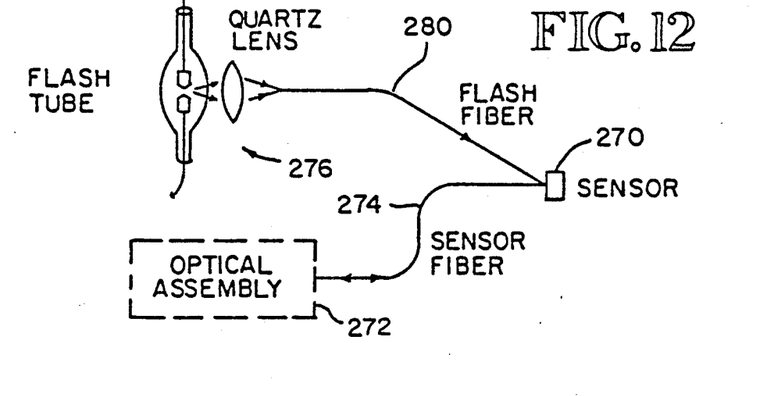
FIG. 12 is a schematic diagram of one embodiment of the optical components used with a system to measure the concentration of oxygen in blood.
Figure 13:
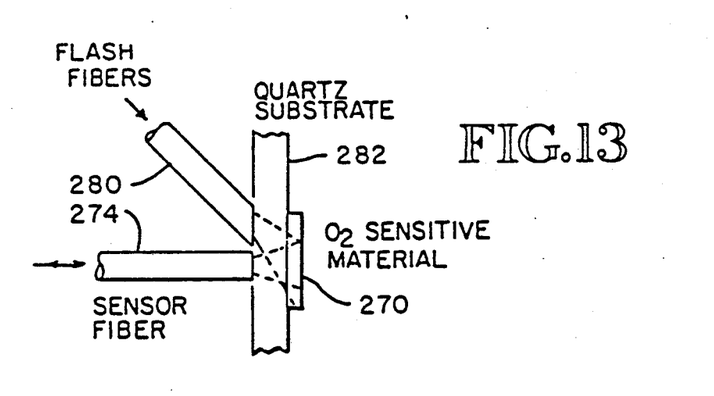
FIG. 13 is a close-up detail of the connection of the optical conductors to the sensor of FIG. 12.

A first method of coupling light from xenon flash 276 to sensor 270 is shown in FIG. 12. This method uses one or more flash fibers 280 to transmit the flash light to sensor 270. The amount of flash light transmitted to sensor 270 is thus a function of the number of flash fibers 280 that are used. FIG. 13 shows a closeup view of the configuration of sensor 270, shown in FIG. 12. Flash light received from flash fibers 280 is refracted by quartz substrate 282 in order to illuminate the viologen in sensor 270. Light produced by the LED is transmitted and received along sensor fiber 274, which connects to optics assembly 220.

Figure 14:
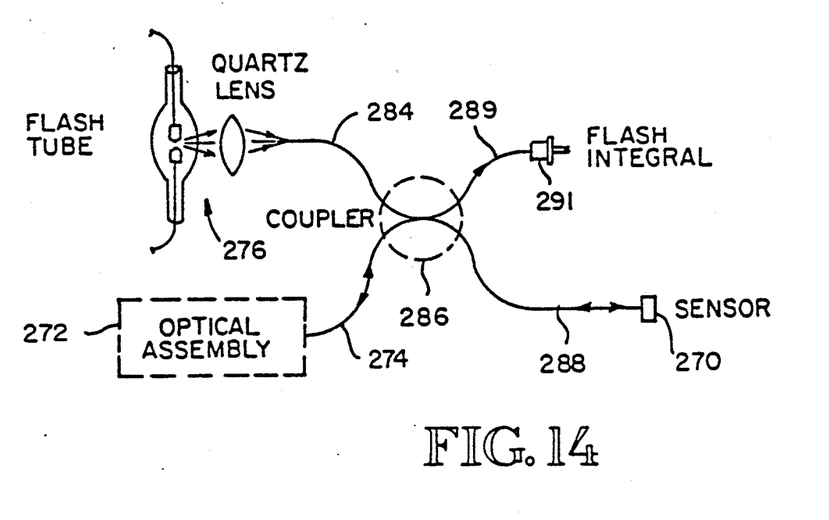
FIG. 14 is another embodiment of the optical components used in a system to measure the concentration of oxygen in blood.

In another embodiment, shown in FIG. 14, xenon light is coupled to sensor 270 through flash fiber 284, which connects to fused fiber coupler 286. Optical assembly 220 is also connected to fused fiber coupler 286 through fiber optic 274. The LED light produced by optical assembly 220 passes through optical fiber 274, fused fiber coupler 286, and optical fiber 288 before reaching sensor 270. LED light returns from sensor 270 along the same path. Light from xenon flash 276 reaches fused fiber coupler 286 through fiber optic 284. The xenon light is then transmitted to sensor 270 along fiber optic 288. In this embodiment, the xenon flash light illuminates the same region of the oxygen sensor 270 as the interrogating LED light. The xenon light which reaches sensor 270 is somewhat reduced because of light losses at fused fiber coupler 286. The other leg 289 of the fused coupler can be used to monitor and maintain total flash energy at a reasonably constant level, as discussed earlier. Photocurrent from photodiode 291 is integrated during the flash period using electronic circuity, as previously described. When diode 291 is used, the beam splitter 254 and photodiode 258 of optics assembly 220 (FIG. 11) may be eliminated.

Figure 18:
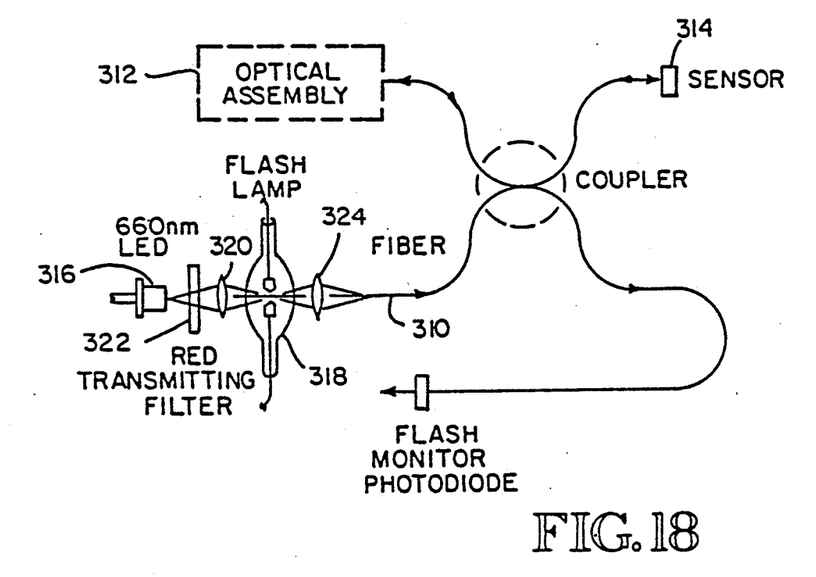
FIG. 18 is a schematic diagram of yet another embodiment of the optical components used in a system to measure the concentration of oxygen in blood.

The schematic diagram of FIG. 18 shows yet another embodiment of the optical components in a system used to measure the concentration of oxygen in blood. With this LED-through-flash-lamp design, optical fiber 310 carries both signals from LED 316 and flash lamp 318. The signals from the flash lamp 318, which is located at the focal plane of optical components 320, are received by optical fiber 310 and transmitted to sensor 314. The reflected signals are returned to optics assembly 312 in the manner described above. Signals from LED 316 (for example, a 660 nm LED) are transmitted through red transmitting filter 322 and focused at the focal plane of lens 320. Thereafter, the light is focused by lens 324 onto optical fiber 310 to produce the desired LED signal to sensor 314.

Figure 15:
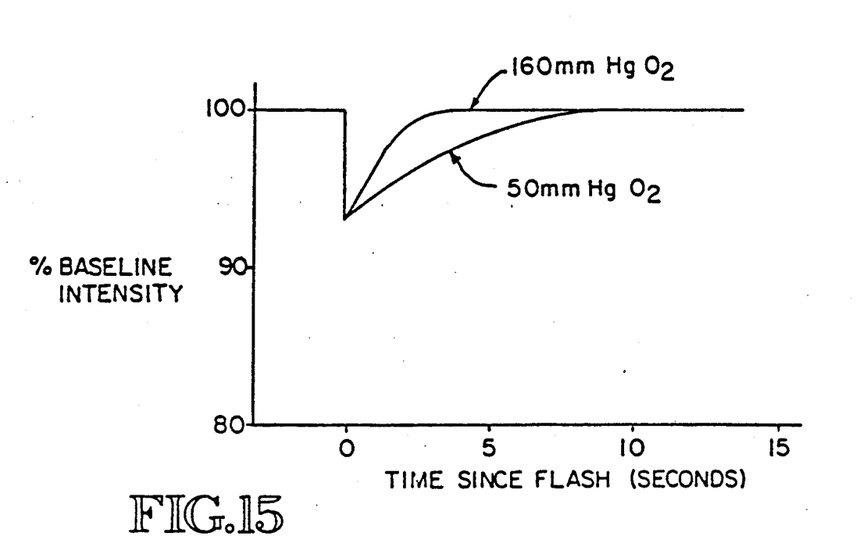
FIG. 15 is a plot of the typical time response of an oxygen sensor of the present invention, shown as a function of partial pressure of oxygen.
Figure 16:
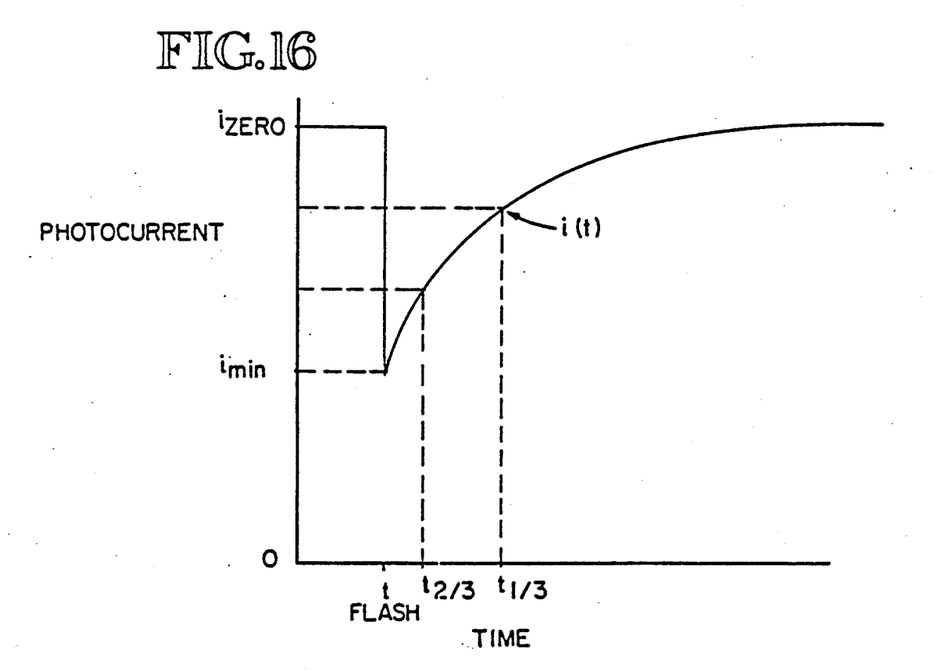
FIG. 16 is a plot showing the characteristics of the time response of the oxygen sensor of the present invention.
Figure 17:
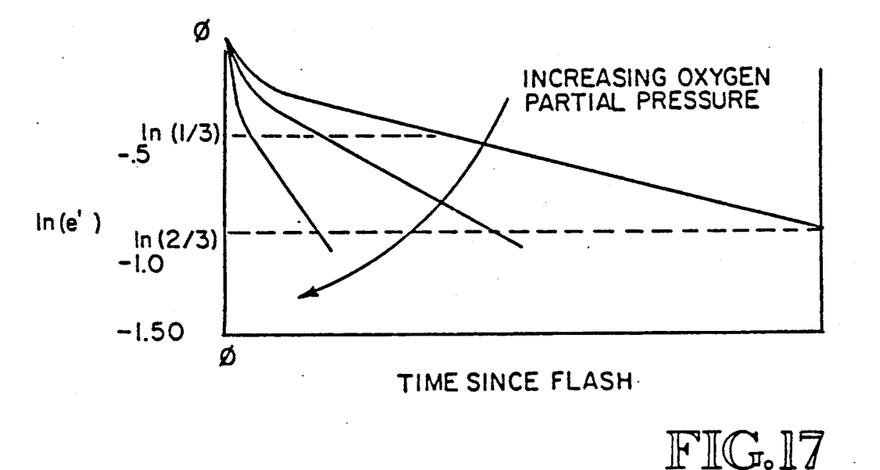
FIG. 17 is a plot of the time response of the oxygen sensor of the present invention, shown as a function of oxygen partial pressure.

Absorption decay curves for a typical viologen/polymer film sensor are shown in FIG. 15. The time constant of this film is on the order of seconds. It has been found that, in order to obtain sufficient light levels to activate the viologen indicator in the oxygen sensor, the flash lamp should be filled with xenon at a pressure of 1 to 10 atmospheres. Turning to FIG. 16, which shows the photocurrent produced by a $pO_2$ sensor of the present invention in response to a xenon light pulse, it can be seen that the time response of the $pO_2$ sensor can be determined by making only two measurements. FIG. 17 shows the transient characteristics of the photocurrent returning from an oxygen sensor that has been exposed to a xenon flash. Where $i_{zero}$ is the photocurrent in the absence of ultraviolet light and $i_{min}$ is the photocurrent immediately after the oxygen sensor has been exposed to a xenon flash, the absorption of the oxygen sensor can be measured by the parameter $e'$, where $e' = -(i(t)-i_{zero})/(i_{zero}-i_{min})$. Computing the variable ln( ) as a function of time since the xenon flash, the oxygen sensor response can be seen to follow straight lines that are characteristic of the partial pressure of oxygen in the blood sample. It should be noted that for thin films, this measurement is independent of flash energy or LED intensity and represents oxygen partial pressure independently of the magnitude of $i_{min}$ in FIG. 16. This is because the decolorization in thin films (0.5 to 2.0 microns) is predominantly controlled by diffusion of oxygen into the uniformly activated film.

Figure 19:
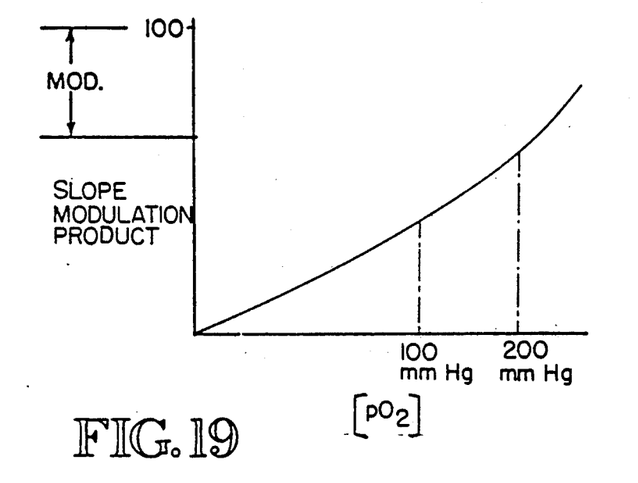
FIG. 19 is a plot of the product of exponential slope factor and modulation ratio as a function of $pO_2$.

If the film thickness is increased substantially (5–8 microns) and/or the degree of viologen cross-linking is high, the exponential decay parameter is not the only factor useful for monitoring $pO_2$ partial pressure. For optically thick films washed in 100 mM saline at 90° C. for 48 hours, it has been found that (a) the photosensitivity increases by a factor of two, and (b) the parameter also depends strongly on the flash energy. By maintaining a constant flash energy, the parameter can still be used as a measure of $pO_2$. However, for these thick films it has been found that a more robust correlation for $pO_2$ is the product of and the modulation ratio, $(i_{zero}-i_{min})/i_{zero}$. By inclusion of the modulation ratio, the effect of flash energy is virtually eliminated for all sensor films. Furthermore, the slope-modulation product so defined increases in a near-linear fashion with increased $pO_2$ (FIG. 19).

Figure 20:
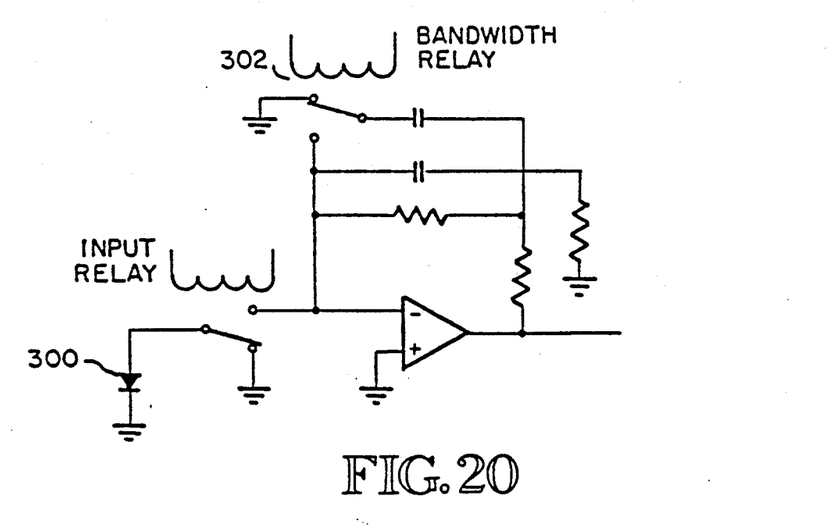
FIG. 20 is a schematic diagram of an electronic circuit for switching the bandwidth of the detection circuit.

During the flash period, photodiode 300 (FIG. 20) is disconnected to avoid a large photocurrent transient caused by the flash's long-wavelength output. To obtain the most accurate measurement of the viologen absorbance decay process after the flash, the switched bandwidth detection circuit shown in FIG. 20 can be used. The circuit comprises an operational amplifier having photodiode 300 switchable into its input circuit and having switchable feedback capacitance to decrease the resulting bandwidth. Immediately after the flash, upon reconnection of photo diode 300, wide-bandwidth amplification corresponding to time constant $R_{Fb}C_{Fs}$ is used for a short period to slew the output to the initial output photovoltage. After the output has stabilized, the second capacitor $C_{ls}$ is switched in by bandwidth relay 302 to decrease the bandwidth and increase the signal-to noise ratio during logging of the comparatively slow absorbance decay process.

What is claimed is:

1. A sensing system for measuring the concentration of a reducing or oxidizing species in a fluid sample, comprising:
   a source of a first radiation having predetermined spectral characteristics;
   a source of a second radiation having a predetermined spectral characteristic that is different from a spectral characteristic of said first radiation;
   an indicator means disposed so that said first and second radiation can illuminate said indicator means, said indicator means having optical characteristics such that during or after illumination with said second radiation, the rate of change in an optical characteristic of said first radiation after illuminating said indicator means is a function of the concentration of said species to which said indicator means is exposed; and
   measurement means for measuring the change in said optical characteristic of said first radiation and generating a signal corresponding thereto.

2. The sensing system of claim 1 wherein said optical characteristic is the absorption of said first radiation by said indicator means after said first radiation has passed through said indicator means.

3. The sensing system of claim 1 wherein said indicator means is disposed in an indicator chamber in optical communication with said sources of first and second radiation.

4. The sensing system of claim 3 wherein said indicator chamber includes a radiation-transmissive wall receiving said first and second radiation, and a radiation-reflective wall facing the transmissive wall with said indicator means positioned therebetween for reflecting said first radiation transmitted through said indicator means from said radiation-transmitted through said indicator means from said radiation-transmissive wall whereby said first radiation is transmitted through said indicator means, reflected from said radiation-reflective wall back through said indicator and said radiation-transmissive wall to said measurement means.

5. The sensing system of claim 4 wherein the reflective wall of said indicator chamber is a mirror having an aperture to allow said sample to pass through said mirror into said indicator chamber.

6. The sensing system of claim 5 wherein said aperture is in the form of a pair of elongated parallel slots in said mirror forming a reflecting bar therebetween.

7. The sensing system of claim 5 wherein said mirror is fabricated by wet chemistry micromachining a sheet of reflective material.

8. The sensing system of claim 7 wherein said material is single-crystal silicon.

9. The sensing system of claim 7 wherein said mirror has formed therein a plurality of microminiature apertures.

10. The sensing system of claim 5 wherein said mirror is formed from a sheet of thin film porous media coated with a reflective substance.

11. The sensing system of claim 1 wherein the indicator means is a viologen film.

12. A sensor for measuring the concentration of a reducing or oxidizing species in a fluid sample, comprising:
   an indicator chamber in communication with said sample; and
   indicator means mounted in said indicator chamber so that radiation entering said chamber illuminates said indicator means, said indicator means having optical characteristics such that, after illumination with a second radiation having predetermined spectral characteristics, the rate of change in an optical characteristic of a first radiation having a spectral characteristic that is different from a spectral characteristic of said second radiation after illuminating said indicator means is a function of the concentration of said species to which said indicator means is exposed.

13. The sensor of claim 12 wherein said optical characteristic is the absorption of said first radiation by said indicator means after said first radiation has passed through said indicator means.

14. The sensor of claim 10 wherein the indicator means is an oxygen-sensitive viologen.

15. The sensor of claim 10 wherein said indicator chamber includes a radiation-transmissive wall adapted to receive said first and second radiation, and a radiation-reflective wall facing the transmissive wall with said indicator means positioned therebetween for reflecting said first radiation transmitted through said indicator means from said radiation-transmissive wall whereby said first radiation is transmitted through said indicator means, reflected from said radiation-reflective wall back through said indicator and said radiation-transmissive wall.

16. The sensor of claim 15 wherein the reflective wall of said indicator chamber is a mirror having an aperture to allow said sample to pass through said mirror into said indicator chamber.

17. The sensor of claim 16 wherein said aperture is in the form of a pair of elongated parallel slots in said mirror forming a reflecting bar therebetween.

18. The sensor of claim 16 wherein said mirror is fabricated by wet chemistry micromachining a sheet of single-crystal silicon.

19. The sensor of claim 16 wherein said mirror has formed therein a plurality of microminiature apertures.

20. The sensor of claim 16 wherein said mirror is formed from a sheet of thin film porous media coated with a reflective substrate.

21. A method of sensing the concentration of a reducing or oxidizing species in a fluid sample, comprising:
providing a first radiation having predetermined spectral characteristics;
providing a second radiation having a predetermined spectral characteristic that is different from a spectral characteristic of said first radiation;
exposing an indicator to said sample, said indicator having optical characteristics responsive to said first radiation such that during or after illumination with said second radiation, the rate of change in an optical characteristic of said first radiation after illuminating said indicator is a function of the concentration of said species to which said indicator means is exposed;
illuminating said indicator with said second radiation;
during or after illuminating said indicator with said second radiation, illuminating said indicator with said first radiation; and
measuring the optical characteristic of said first radiation in said indicator after said indicator has been illuminated by said second radiation, thereby allowing the concentration of said species in said sample to be determined.

22. The method of claim 21 wherein said optical characteristic is the absorption of said first radiation by said indicator means after said first radiation has passed through said indicator means.

23. The method of claim 21 wherein said indicator is a film containing an oxygen-sensitive viologen.

* * * * *